United States Patent [19]

Wentzheimer et al.

[11] 4,198,530

[45] Apr. 15, 1980

[54] PRODUCTION OF TERTIARY BUTYL METHYL ETHER

[75] Inventors: W. Wayne Wentzheimer, Glen Mills; Frank W. Melpolder, Wallingford, both of Pa.

[73] Assignee: Atlantic Richfield Company, Los Angeles, Calif.

[21] Appl. No.: 912,622

[22] Filed: Jun. 29, 1978

[51] Int. Cl.$^2$ .................. C07C 41/06; C07C 41/10; C07C 41/12

[52] U.S. Cl. .................................. 568/697; 568/699

[58] Field of Search .................. 260/614 A, 616; 568/697, 699

[56] References Cited

U.S. PATENT DOCUMENTS

| | | | |
|---|---|---|---|
| 2,480,940 | 9/1949 | Leun et al. | 260/614 A |
| 3,119,766 | 1/1964 | Voltz et al. | 260/614 A |
| 3,940,450 | 2/1976 | Lee | 260/616 X |
| 3,979,461 | 9/1976 | Ancillotti et al. | 568/697 |
| 4,039,590 | 8/1977 | Ancillotti et al. | 260/614 A |
| 4,090,885 | 5/1978 | Lyons | 260/614 A |

FOREIGN PATENT DOCUMENTS

| | | | |
|---|---|---|---|
| 2629769 | 1/1978 | Fed. Rep. of Germany | 260/614 A |
| 2312483 | 12/1976 | France | 260/614 A |
| 957000 | 4/1964 | United Kingdom | 260/614 A |
| 1176620 | 1/1970 | United Kingdom | 260/614 A |
| 1369889 | 10/1974 | United Kingdom | 260/614 A |

*Primary Examiner*—Howard T. Mars
*Attorney, Agent, or Firm*—John R. Ewbank

[57] ABSTRACT

A mixed C$_4$ hydrocarbon stream containing from 5 to 60% isobutene is mixed with methanol providing from about 2% to about 20% excess methanol (stoichiometry based on isobutene content) to provide fresh feed for preparing tertiary butyl methyl ether in a reaction zone containing acidic ion exchange catalyst. Formation of trouble-some amounts of diisobutylene is repressed by the presence of the excess methanol. The effluent comprising TBME, excess methanol, and unreacted C$_4$ hydrocarbons is directed to a unique purification zone. The butenes are distilled from the effluent at a pressure from about 7 to 25 atmospheres, preferably at about 12 to 20 atmospheres. Surprisingly all of the excess methanol is azeotropically removed with the C$_4$ hydrocarbons by the pressurized azeotropic distillation, leaving a bottoms consisting of a technical grade of TBME free from troublesome amounts of methanol.

2 Claims, 4 Drawing Figures

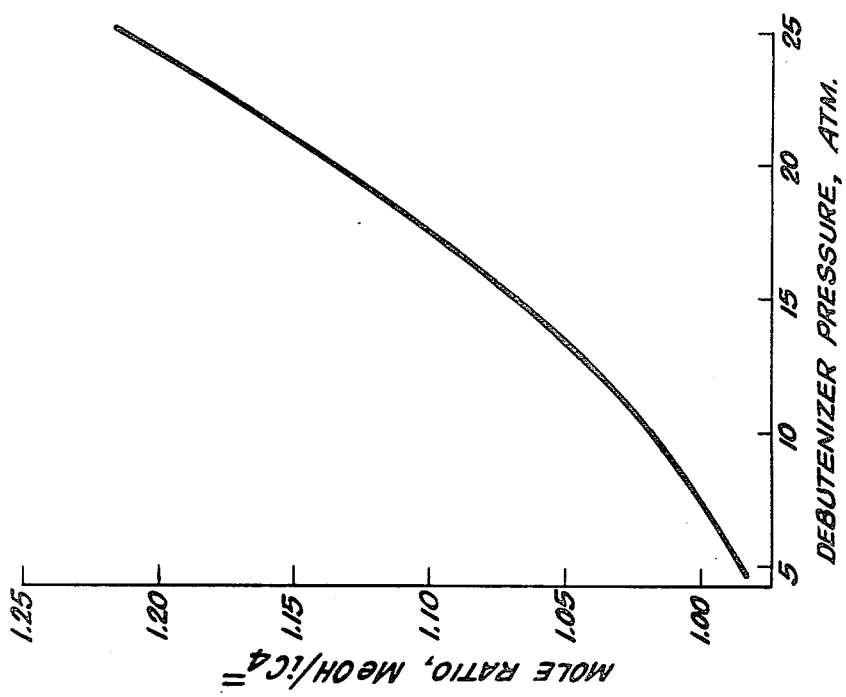
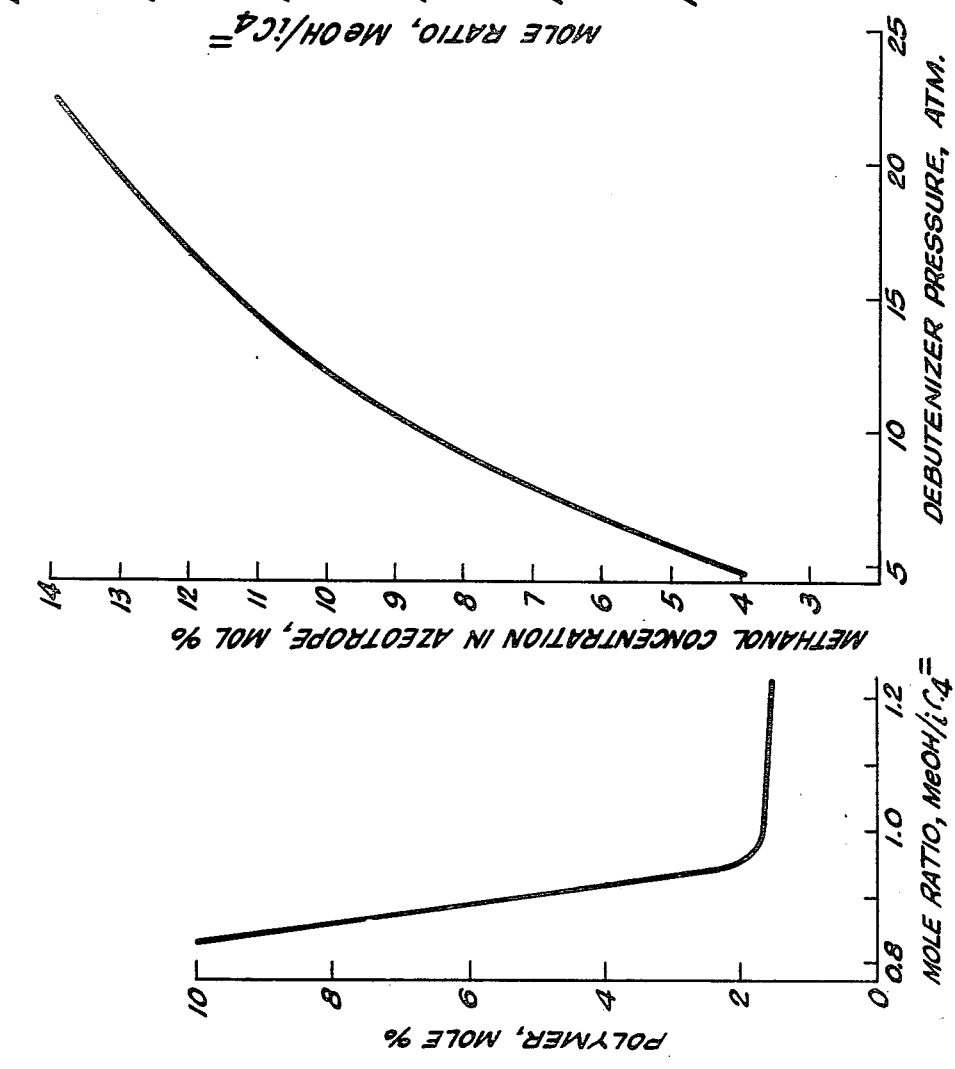

PRODUCTION OF TERTIARY BUTYL METHYL ETHER

FIELD OF INVENTION

This invention relates to manufacture of tertiary butyl methyl ether, the repression of the propensity for the formation of diisobutylene and/or triisobutylene and the purification of the crude product.

PRIOR ART

Leum et al U.S. Pat. No. 2,480,940 describes the use of acidic ion exchange catalyst for selectively etherifying tertiary olefins with an alcohol. Haunschild U.S. Pat. No. 3,629,478 describes the use of such ion exchange resin as a clean-up reactor for a two stage preparation of tertiary butyl methyl ether. Openaus et al West German Offenlegungschrift 2,629,769 published Jan. 5, 1978 describes the azeotropic separation of methanol from TBME by conducting the azeotropic distillation at an elevated pressure subsequent to the atmosphere pressure separation of the unreacted $C_4$ hydrocarbons from the effluent from a reactor. Such German patent stresses the characteristics of the azeotrope formation of TBME and methanol.

Notwithstanding the many man hours devoted to research concerning the preparation of TBME by many organizations over a period of many decades, there has continued to be a long-standing demand for preparing TBME free from troublesome amounts of diisobutylene, methanol and related impurities.

SUMMARY OF THE INVENTION

In accordance with the present invention, a pressure in the range from about 7 to 25 atmospheres is employed in the separation of the unreacted $C_4$ hydrocarbons from the effluent from a zone for preparing TBME. The reaction mixture is controlled to contain from 2 to 20% excess methanol to repress formation of diisobutylene, triisobutylene, and other undesired by-products.

DESCRIPTION OF DRAWINGS

FIG. 1 is a graph schematically showing the correlation of formation of polymer as there is a change in the mol ratio of methanol to isobutylene.

FIG. 2 is a graph schematically showing the correlation of concentration of the methanol-butene azeotrope as there is a change in pressure.

FIG. 3 is a graph schematically showing the correlation of debutenizer pressure required to remove all of the methanol from the tertiary butyl methyl ether as there is a change in the mol ratio of methanol to isobutene at a conversion of about 93% of the isobutene. Somewhat similar curves could show similar relationship for conversions above or below such 93%.

DESCRIPTION OF PREFERRED EMBODIMENTS

Figure 4:
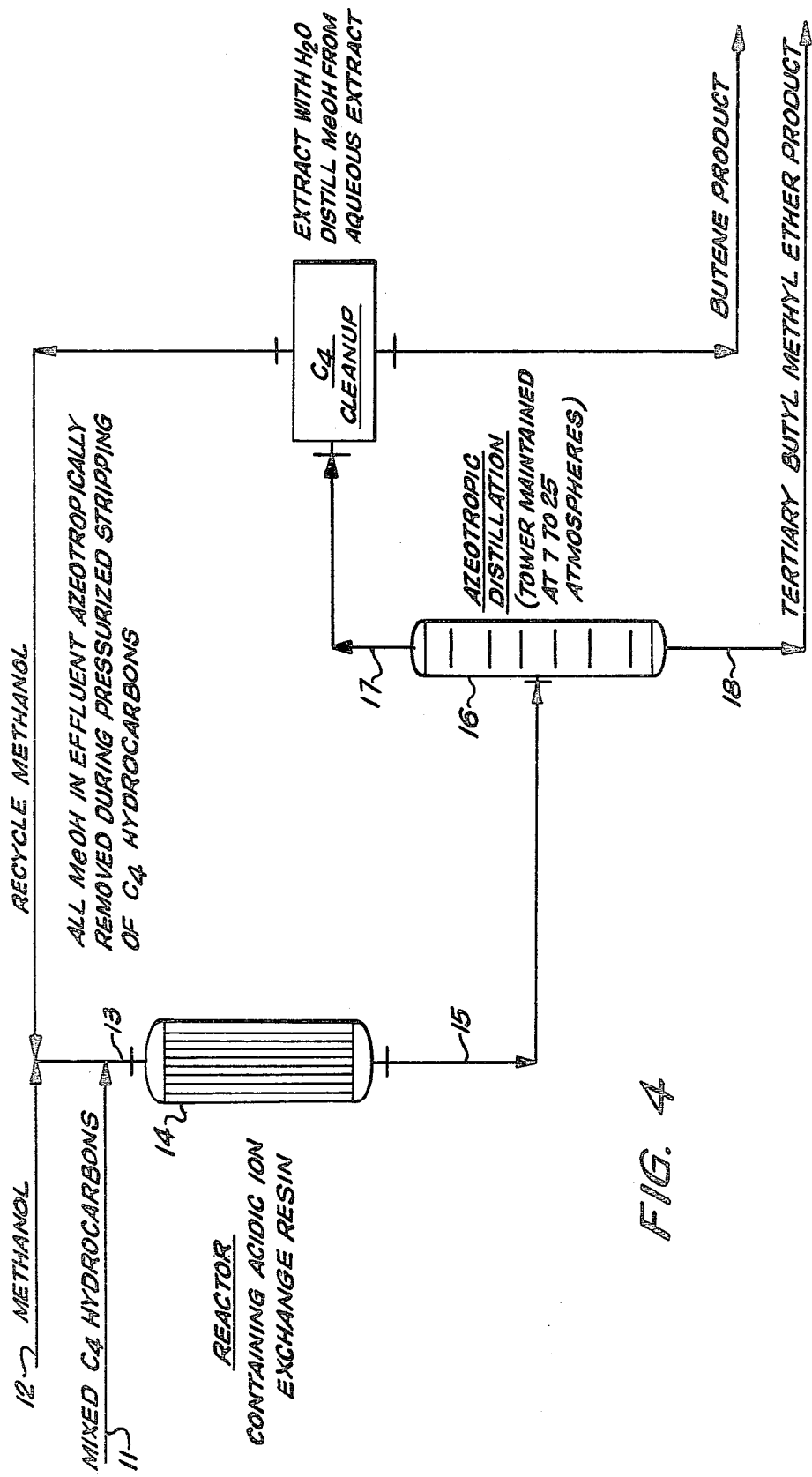
FIG. 4 is a schematic flow sheet for a method of preparing TBME in accordance with the present invention.

As shown in FIG. 4, a $C_4$ hydrocarbon stream 11 desirably consisting of normal butenes and from about 5% to 60% isobutene, is mixed with a controlled amount of a methanol stream 12 to provide a reaction mixture stream 13 featuring a unit mol ratio of methanol to isobutene which is at least 1.02 but not more than 1.20, desirably about 1.03 to about 1.07. Such unit mol ratio range can also be described as from 2 to 20% excess methanol relative to stoichiometric reactant proportions. Particular attention is directed to the repression of the formation of diisobutylene, triisobutylene, etc. because the reaction mixture contains excess methanol. The fresh feed mixture stream 13 containing 2–20% excess methanol is directed into a reactor 14 containing a catalyst bed of ion exchange resin having acidic characteristics. Etherification is conducted at a space rate within a range from about 2 to 20 weights of total feed per weight of dry catalyst per hour. The reactor has an average temperature within a range from about 90° to 170° F. A portion of the reactor effluent can be recirculated as an engineering expedient for temperature control. The effluent stream 15 from the reactor 14 is directed to a pressurized azeotropic distillation zone 16 maintained at a pressure within the range from 7 to 25 atmospheres preferably 12 to 20 atmospheres. The azeotropic distillate stream 17 features a mixture of normal butenes and methanol constituting from about 5 to about 15% of the molar concentration of the mixture of methanol and $C_4$ hydrocarbon content. Any unreacted isobutene is thus a part of the distillate. Of particular importance, the bottoms stream 18 consists of high purity tertiary butyl methyl ether having no troublesome concentrations of (i.e. substantially free from) methanol, whereby the TBME does not require a water wash prior to use as a fuel component in gasoline.

The peak temperature for the distillation can be lower than if attempts were made to distill any of the TBME at such pressure.

In various modifications of the invention it is feasible to vary the mol ratio methanol to isobutene from about 1.02 to about 1.2 (that is, from about 2% to about 20% excess) while still retaining many of the advantages of the present invention. It is important that there be a sufficient amount of excess methanol in the reaction mixture to repress the formation of diisobutylene or triisobutylene. FIG. 1 shows the significant increase in polymer formation if there is a significant decrease in the ratio of methanol to butenes. Moreover it is desirable to maintain the excess methanol in order to promote formation of tertiary butyl methyl ether at a favorable space rate at an attractive temperature. It is not necessary to attain the theoretical equilibrium concentration of tertiary butyl methyl ether, inasmuch as the goal is to achieve a reasonable conversion at a reasonable selectivity while still providing as high a space rate and small a reactor as plausible for good engineering practice.

The reactor can be provided with a temperature control system for appropriate engineering control. The percent selectivity of the isobutene to the tertiary butyl methyl ether product is quite favorable as long as the methanol to isobutene unit molar ratio in the fresh feed is within the required range from 1.02 to 1.20.

A large amount of excess methanol should not be used because such excess would not be completely removed by the azeotropic distillation of the butenes therefrom. If the concentration of the isobutene in the fresh feed $C_4$ hydrocarbon stream is so large that the utilization of the 1.2 mol ratio of methanol would not permit azeotropic removal of all of the unreacted excess methanol with the unreacted butenes, a portion of the butenes can be recycled so that the concentration of the isobutene in the total feed $C_4$ hydrocarbon stream does not exceed about 60%. Excessive costs are incurred if the isobutene concentration in the total $C_4$ hydrocarbon feed is below 5%, so the operable range is 5% to 60%.

It should be noted from the graphs of FIGS. 1, 2 and 3, that increased pressure increases the concentration of methanol in the azeotrope, a surprising discovery. Moreover at a suitable conversion, the effect of unit mol ratio of reactants and the effect of pressure in the azeotropic distillation zone can be selected to assure substantially complete removal of the methanol from the withdrawn bottoms stream consisting of a technical grade of tertiary butyl methyl ether. The flow sheet of FIG. 4 is predominantly self explanatory. In cleaning up the $C_4$ hydrocarbon distillate, the methanol is extracted from the hydrocarbon by water washing and the methanol is recycled. Distillation permits recovery of the methanol for such recycling.

In a preferred embodiment, the fresh $C_4$ hydrocarbons contain 40% isobutene and there is no recycle of reactor effluent. The methanol concentration represents a 7% excess beyond stoichiometric proportions. The reactor is maintained at an average temperature of 150° F. at a space rate of 7 weights of total feed per weight of Dowex 50 acidic ion exchange resin per hour. The effluent flows to a distillation tower maintained at about 20 atmospheres pressure. Most portions of the system are maintained under pressures in the 21-19 atmospheres range. The azeotropic distillate contains about 12% methanol and 88% $C_4$ hydrocarbons. The azeotrope is water washed countercurrently with water corresponding to about 25% water by volume, and the extract is distilled for recovery of methanol suitable for recycling. The tertiary butyl methyl ether withdrawn as bottoms from the azeotropic distillation is adequately purified for use in gasoline, and is substantially free from methanol, whereby no water washing or distillation of the TBME is necessary.

Various modifications of the invention are possible without departing from the scope of the invention as set forth in the amended claims.

The invention claimed is:

1. In the method in which most of the isobutene content of a $C_4$ hydrocarbon stream containing significant amounts of normal butenes selectively reacts with methanol in the presence of an acidic ion exchange resin catalyst to form tertiary butyl methyl ether, in which tertiary butyl methyl ether is withdrawn as one of the products of the process, and in which a mixture of methanol and $C_4$ hydrocarbons is distilled at super atmospheric pressure to provide a residue comprising tertiary butyl methyl ether, the improvement which consists of:

controlling the concentration of the isobutene in the $C_4$ hydrocarbon stream to be more than 5% but less than 60% by weight of the $C_4$ hydrocarbon stream portion of the total feed;

providing a total feed having a unit mol ratio of methanol to isobutene which is within the range from 1.02 to 1.20, thereby significantly repressing formation of diisobutylene in the reactor;

directing a total feed mixture comprising methanol, isobutene and other $C_4$ hydrocarbons, said total feed having the required unit mol ratio of methanol to isobutene within the range from 1.02 to 1.20 through a reactor containing an acidic ion exchange catalyst at a temperature within the range from 90° to 170° F. at an hourly weight velocity within the range from about 2 to about 20 to prepare an effluent comprising tertiary butyl methyl ether, $C_4$ hydrocarbons, and excess methanol;

transferring the effluent from the reactor to an azeotropic distillation zone, and there distilling the $C_4$ hydrocarbons from the effluent at a pressure within the range from 12 atmospheres to 25 atmospheres, whereby substantially all of the methanol in said effluent is azeotropically removed together with the $C_4$ hydrocarbons and whereby substantially all of the methanol is removed from the tertiary butyl methyl ether;

washing the $C_4$ hydrocarbon distillate with an aqueous extractant to provide a cleaned up $C_4$ hydrocarbon stream free from methanol;

recovering methanol from said aqueous extractant and directing the recovered methanol as recycle to said reactor containing an acidic ion exchange;

and removing the purified tertiary butyl methyl ether as the bottom stream from the pressurized azeotropic distillation zone.

2. In the method in which most of the isobutene content of a $C_4$ hydrocarbon stream containing significant amounts of normal butenes selectively reacts with methanol in the presence of an acidic ion exchange resin catalyst to form tertiary butyl methyl ether, in which tertiary butyl methyl ether is withdrawn as one of the products of the process, and in which a mixture of methanol and $C_4$ hydrocarbons is distilled at super atmospheric pressure to provide a residue comprising tertiary butyl methyl ether, the improvement which consists of:

controlling the concentration of the isobutene in the $C_4$ hydrocarbon stream to be more than 5% but less than 60% by weight of the $C_4$ hydrocarbon stream portion of the total feed;

providing a total feed having a unit mol ratio of methanol to isobutene which is within the range from 1.02 to 1.20, thereby significantly repressing formation of diisobutylene in the reactor;

directing a total feed mixture comprising methanol, isobutene and other $C_4$ hydrocarbons, said total feed having the required unit mol ratio of methanol to isobutene within the range from 1.02 to 1.20 through a reactor containing an acidic ion exchange catalyst at a temperature of about 150° F. at an hourly weight velocity of about 7 to prepare an effluent comprising tertiary butyl methyl ether, $C_4$ hydrocarbons, and excess methanol;

transferring the effluent from the reactor to an azeotropic distillation zone, and there distilling the $C_4$ hydrocarbons from the effluent at a pressure of about 20 atmospheres, whereby substantially all of the methanol in said effluent is azeotropically removed together with the $C_4$ hydrocarbons and whereby substantially all of the methanol is removed from the tertiary butyl methyl ether;

washing the $C_4$ hydrocarbon distillate with an aqueous extractant to provide a cleaned up $C_4$ hydrocarbon stream free from methanol;

recovering methanol from said aqueous extractant and directing the recovered methanol as recycle to said reactor containing an acidic ion exchange;

and removing the purified tertiary butyl methyl ether as the bottom stream from the pressurized azeotropic distillation zone.

* * * * *